(12) United States Patent
Carr et al.

(10) Patent No.: US 8,470,260 B2
(45) Date of Patent: Jun. 25, 2013

(54) LIGHT BEAM GUIDED LIQUID DELIVERY DEVICE

(75) Inventors: David Andrew Carr, Charlotte, NC (US); Jennifer W. Weller, Charlotte, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 13/264,768

(22) PCT Filed: Apr. 21, 2010

(86) PCT No.: PCT/US2010/031823
§ 371 (c)(1),
(2), (4) Date: Oct. 17, 2011

(87) PCT Pub. No.: WO2010/123951
PCT Pub. Date: Oct. 28, 2010

(65) Prior Publication Data
US 2012/0033232 A1    Feb. 9, 2012

Related U.S. Application Data

(60) Provisional application No. 61/171,496, filed on Apr. 22, 2009.

(51) Int. Cl.
*G01B 11/14*    (2006.01)
(52) U.S. Cl.
USPC ........... 422/501; 422/516; 422/517; 422/518; 422/520; 422/922; 422/923; 422/924; 422/925; 422/926; 422/927; 422/928; 422/929; 436/180; 73/1.74; 73/863.32; 73/864.01

(58) Field of Classification Search
USPC .............. 436/180; 422/501, 516, 517, 518, 422/520, 922–929; 73/1.74, 863.32, 864.01–864.24
See application file for complete search history.

(56) References Cited

U.S. PATENT DOCUMENTS

| | | | | |
|---|---|---|---|---|
| 5,271,902 A | * | 12/1993 | Sakka et al. | 422/511 |
| 5,758,448 A | * | 6/1998 | Thummel | 42/114 |
| 5,772,578 A | | 6/1998 | Heimberger et al. | |
| 5,810,841 A | | 9/1998 | McNeirney et al. | |
| 5,919,706 A | * | 7/1999 | Tajima | 436/54 |
| 6,100,094 A | * | 8/2000 | Tajima | 436/54 |
| 6,286,219 B1 | | 9/2001 | Palumbo, II | |
| 6,301,997 B1 | | 10/2001 | Welte | |
| 6,499,247 B1 | * | 12/2002 | Peterson | 42/116 |
| 6,761,171 B2 | | 7/2004 | Totl et al. | |
| 6,810,595 B2 | | 11/2004 | Chan | |

(Continued)

FOREIGN PATENT DOCUMENTS

GB    842769    * 12/1958

*Primary Examiner* — Jill Warden
*Assistant Examiner* — Shogo Sasaki
(74) *Attorney, Agent, or Firm* — Hammer & Associates, P.C.

(57) ABSTRACT

A light beam guided liquid delivery device for tracking the placement of a sample by a liquid delivery device into a receptacle like a milliliter or microliter scale tube, or a microtiter plate, includes a liquid delivery device and a light beam generator. The light beam generator may be positioned on the outside or inside of the liquid delivery device. The light beam generator may be adapted to shoot a light beam below the tip of the liquid delivery device, whereby, a user may track the placement of the tip of the liquid delivery device via the light beam.

10 Claims, 5 Drawing Sheets

U.S. PATENT DOCUMENTS

| | | |
|---|---|---|
| 7,186,007 B1 * | 3/2007 | Rotwitt .................. 362/287 |
| 7,331,113 B1 | 2/2008 | Patrick et al. |
| 7,464,478 B2 | 12/2008 | Adrian |
| 2002/0122655 A1 | 9/2002 | Pruefer |
| 2005/0117342 A1 * | 6/2005 | Perlo et al. .................. 362/253 |
| 2005/0171408 A1 | 8/2005 | Parker |
| 2006/0268276 A1 * | 11/2006 | Tajima .................. 356/436 |
| 2007/0044365 A1 * | 3/2007 | Deken .................. 42/146 |
| 2007/0227271 A1 | 10/2007 | Curtis et al. |
| 2009/0165313 A1 | 7/2009 | Borinato |
| 2009/0241357 A1 | 10/2009 | Raschella et al. |
| 2010/0167412 A1 * | 7/2010 | Xiao et al. .................. 436/171 |

\* cited by examiner

US 8,470,260 B2

LIGHT BEAM GUIDED LIQUID DELIVERY DEVICE

RELATED APPLICATION

This application claims the benefit of co-pending provisional application Ser. No. 61/171,496 filed Apr. 22, 2009.

FIELD OF THE INVENTION

The invention is directed toward a light beam guided liquid delivery device for tracking the placement of a sample by a liquid delivery device, like a micropipette, into a small receptacle, like a microtiter plate.

BACKGROUND OF THE INVENTION

A liquid delivery device is any device capable of delivering liquid to a specific receptacle. One commonly used liquid delivery device is a pipette. A pipette (also called a pipet, micropipette, pipettor or chemical dropper) is a laboratory instrument used to transport a measured volume of liquid. Pipettes are commonly used in molecular biology as well as medical tests. Pipettes come in several designs, for various purposes having differing levels of accuracy and precision, from single piece glass pipettes to more complex adjustable or electronic pipettes. Many pipette types work by creating a partial vacuum above the liquid-holding chamber and selectively releasing this vacuum to draw up and dispense.

Pipettes that dispense between 1 and 1000 μl are termed micropipettes, while standard pipettes dispense a greater volume of liquid. Two types of micropipettes are generally used: air-displacement pipettes and positive-displacement pipettes. In particular, piston-driven air-displacement pipettes are micropipettes which dispense an adjustable volume of liquid from a disposable tip. The pipette body contains a plunger, which provides the suction to pull liquid into the tip when the piston is compressed and released. The maximum displacement of the plunger is set by a dial or electronic interface on the pipette body, allowing the delivery volume to be set. Whereas, for larger volumes, cylindrical pipettes (such as volumetric or graduated pipettes) are used and driven by a pipette aid http://en.wikipedia.org/wiki/Pipette). Most pipettes are made of borosilicate, aluminosilicate or quartz with many types and sizes of glass tubing being available. Each of these compositions has unique properties which will determine suitable applications (http://en.wikipedia.org/wiki/Micropipette). Most micropipettes have a plastic housing for the air displacement works (see reference number 24 in FIG. 1), a fitting post for a disposable plastic tip where the tips may be provided in a variety of sizes and shapes that are designed around specific applications (see reference number 18 in FIG. 1); fluids are drawn into the tips. In most assays tips are discarded after each individual use, usually via an ejector mechanism.

Many common methods in e.g. molecular biology, combinatorial chemistry, forensic science, clinical diagnostics, biochemical assays, etc. use standard manual micropipetters for the transfer of small volumes of fluid to and from various receptacle, including, but not limited to, standard 2 milliliter, 1.5 milliliter, and 0.5 milliliter disposable plastic sample tubes, the standard 96-well microtiter plate format, 384- and 512-well microtiter plates, PCR individual and strip tubes, and analysis devices such as 1D and 2D gels, LC and HPLC micro vials, etc. In each case, the operator handling the micropipette must carefully track the tip of the micropipette in order to deliver the reagent/solution to the correct location and do so without touching any other location which would cause contamination. Many of the materials are clear or translucent as are most solutions and reagents, providing minimal visual cues. Therefore, there is a strong demand in the industry for a practical solution for a researcher to locate the proper well to be filled or sampled.

The instant invention is designed to address the above mentioned problems.

SUMMARY OF THE INVENTION

The present invention is a light beam guided liquid delivery device for tracking the placement of a sample by a liquid delivery device, like a micropipette, into a receptacle, like a milliliter or microliter scale tube or a microtiter plate. The light beam guided liquid delivery device includes: a liquid delivery device; and a light beam generator. The light beam generator may be positioned on the outside or inside of the liquid delivery device. The light beam generator may be adapted to shoot a light beam below the tip of the liquid delivery device, whereby, a user may track the placement of the tip of the liquid delivery device via the light beam.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF THE INVENTION

Figure 1:
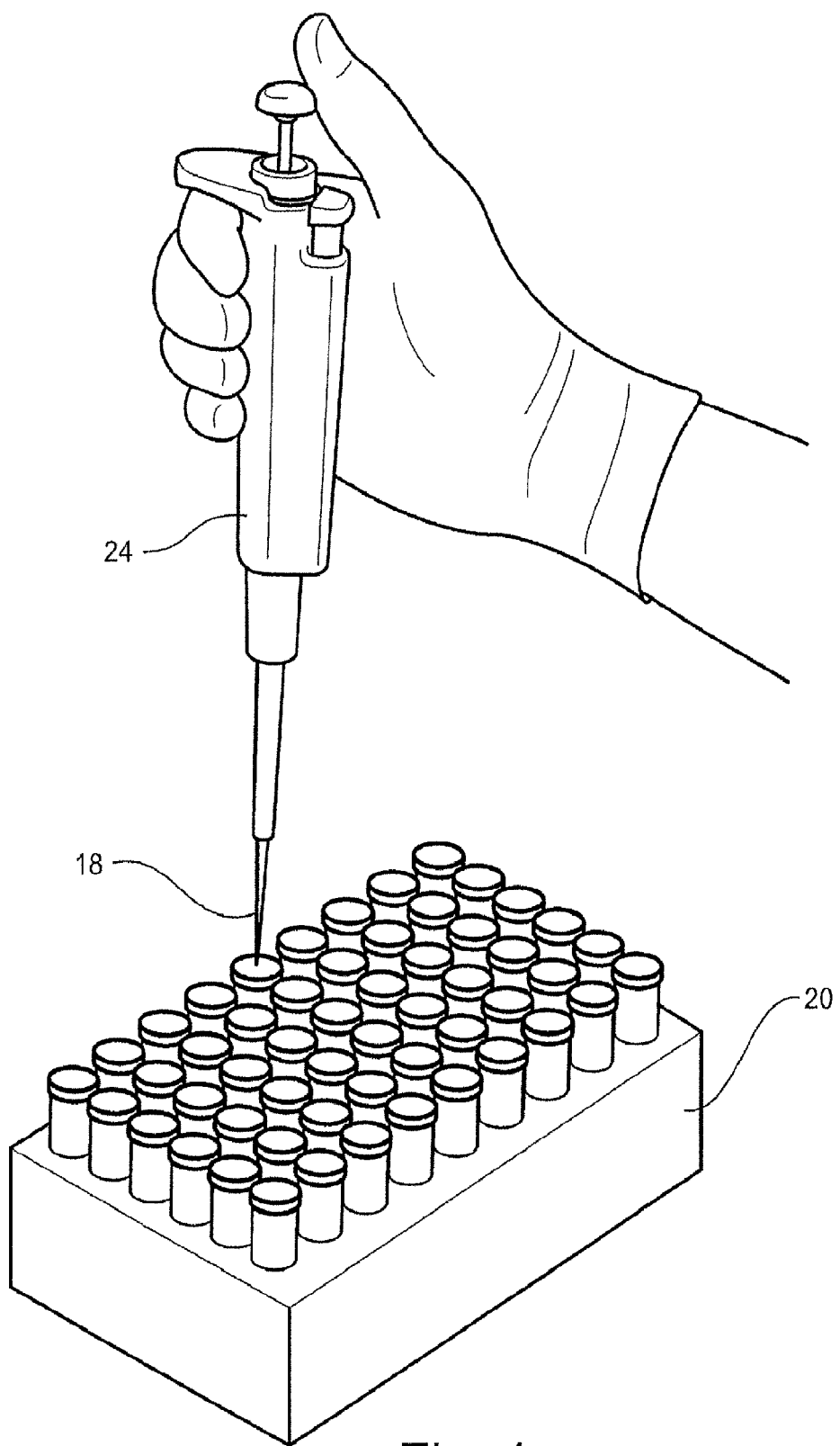
FIG. 1 is an environmental view of a prior art micropipette being used with a microtiter plate.

Referring to the drawings wherein like numerals refer to like elements, there is shown in FIG. 1 a micropipette 24 according to the prior art. Prior to the instant invention, a user of a micropipette would have to guide the tip 18 of micropipette 24 into the small receptacles, or wells, of a microtiter plate 20 by visually guiding tip 18 into the wells. As a result, the operator handling the micropipette must carefully track tip 18 of micropipette 24 in order to deliver the reagent/solution to the correct location and do so without touching any other location which could cause contamination. Many of the materials are clear or translucent as are most solutions and reagents, providing minimal visual cues. The instant invention is designed to aid the operator in tracking the tip 18 of micropipette 24 into the correct location, like the wells of microtiter plate 20.

As used herein the term "well" is a sample holder such as a small test tube where a biological or other sample is placed in microtiter plate 20. Microtiter plate 20 or microplate is a plate that contains multiple wells such as 6, 24, 96, 384, 1536, or more wells.

Referring to FIGS. 2-5, there is shown different embodiments of the instant invention of a light beam guided liquid delivery device 10. Prior to the instant invention, one had to rely on pure eyesight to guide the tip of a liquid delivery device, like a micropipette, into the correct location, like a microtiter plate. See FIG. 1 of the prior art. Light beam guided liquid delivery device 10 may be for tracking the placement of a sample by the liquid delivery device 12 into microtiter plate 14 by lighting up the proper well to insert tip 18. See FIG. 2. Light beam guided liquid delivery device 10 may generally include a liquid delivery device 12 and a light beam generator 14.

Liquid delivery device 12 may be included in the instant invention of light beam guided liquid delivery device 10. See FIGS. 2-5. Liquid delivery device 12 may be any device capable of delivering liquid to a specific receptacle, like a milliliter scale tube, a microliter scale tube or a microtiter plate. Liquid delivery device may be any size, shape, or type of liquid delivery device, including, but not limited to, a pipette or micropipette. A pipette is a slender graduated tube used in a laboratory for measuring and transferring quantities of liquids from one container to another. The pipette may be any type or size of pipette, including a micropipette 24, as shown in FIGS. 1-5. A micropipette or micropipetter is a small pipette for transferring or measuring minute amounts of fluid, microorganisms, etc., with a plastic housing for the fluid uptake and dispensing mechanism. Micropipette 24 is shown in FIGS. 2-5 as a manual micropipette. However, the invention is not so limited, and the laser beam generator 14 could also be positioned outside or inside an electronic micropipette. Micropipette 24 may be a single channel micropipette, as shown in the Figures, but again the invention is not so limited. The instant invention could also be included on a multi-channel micropipette with one or more light beam generators 14 attached for guiding one or more of the tips of the multi-channel micropipette. With multi-channel micropipettes, different color light beams 16 could be used to light up the respective wells for the different channels of the multi-channel micropipette.

Figure 2:
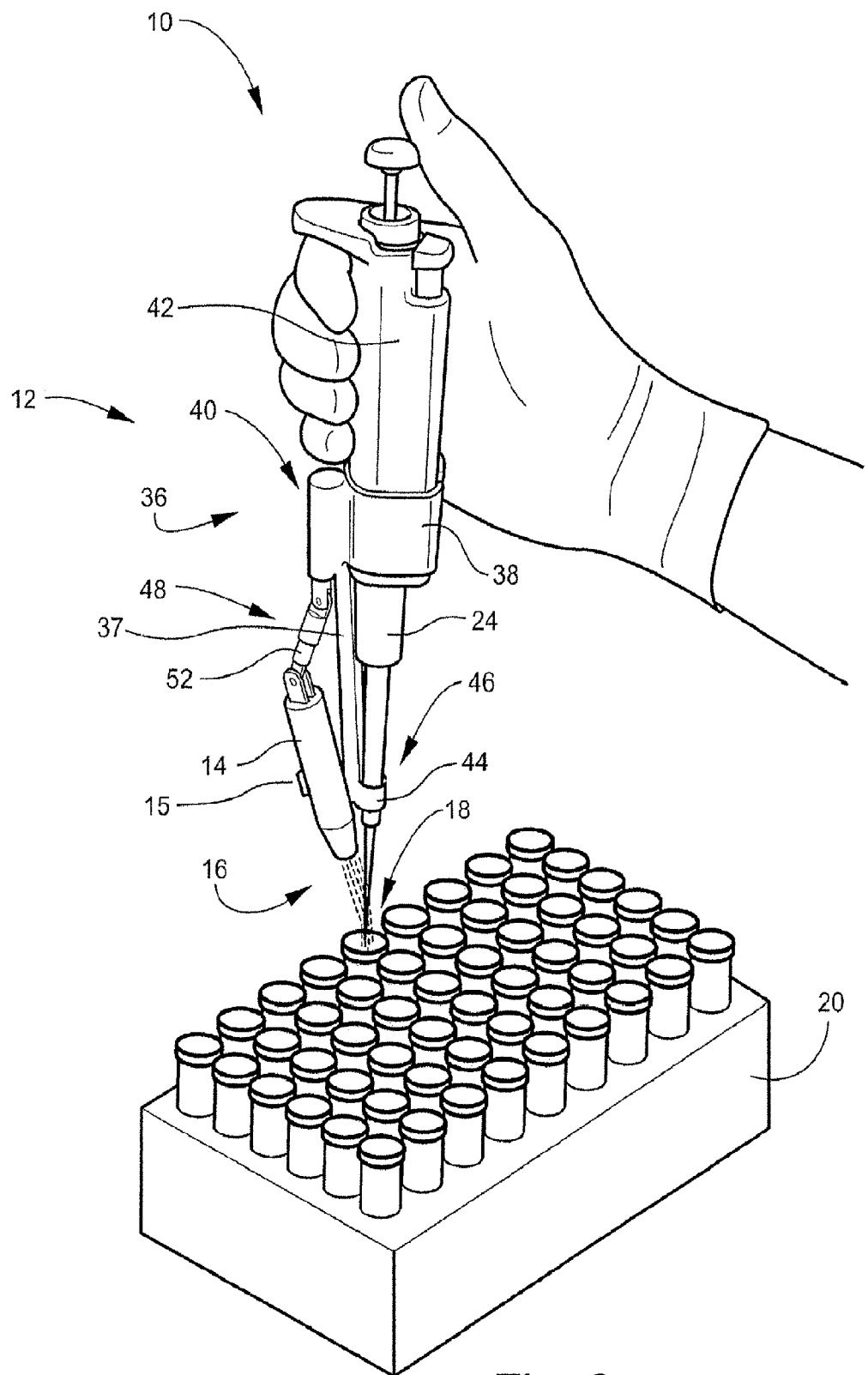
FIG. 2 is an environmental view of one embodiment of the light beam guided liquid delivery device made according to the instant invention being used with a microtiter plate.

Light beam generator 14 may be included in light beam guided liquid delivery device 14. See FIGS. 2-5. Light beam generator 14 may be positioned anywhere on the outside (see FIGS. 2-4) or inside (see FIG. 5) of liquid delivery device 12. Light beam generator 14 may be adapted to shoot light beam 16 below tip 18 of liquid delivery device 12. Light beam 16 being shot below tip 18 may allow a user to track the placement of tip 18 into the correct location, like a well of a microtiter plate, as shown in FIG. 2. Light beam 16 may be aimed to shoot directly below tip 18, or light beam 16 may be aimed directly at the end of tip 18 (see FIG. 4). When light beam 16 is aimed directly at the end of tip 18 as in FIG. 4, tip 18 may deflect light beam 16 downward to light up an area directly below tip 18. In addition, tip 18 may be illuminated while deflecting light beam 16 downward. Thus, both the area directly below tip 18 and tip 18 may be illuminated. Light beam generator 14 may be any device capable of producing a light beam 16. The light beam generator 14 may be provided with any color of light beam 16, including, but not limited to, red, orange, green, blue or yellow. The light beam generator 14 may also be provided with any shape of light beam 16, including, but not limited to, circular, square, triangular, diamond, a cross, a line, or an x-shaped light beam.

Light beam generator 14 may include a button 15 for turning light beam 16 on or off. Button 15 may be included anywhere on light beam guided liquid delivery device 10, including, but not limited to, directly on light beam generator 14, or on channel 42 of micropipette 24. Button 15 may optionally include a timer for turning light beam generator 14 on and off at certain intervals. This feature may be advantageous for enzymes which require the samples to be delivered at specific time intervals.

In one embodiment, light beam generator 14 may be a laser pointer. A laser pointer may be a small laser designed to highlight something of interest by projecting a small bright spot of colored light onto it. Most laser pointers have low enough power that the projected beam presents a minimal hazard to eyes for incidental exposure. The laser beam may not be in itself visible from the side, but may be visible as a result of light scattered by dust particles along the beam path. The small width of the beam and low power of typical laser pointers may make the beam itself invisible in a reasonably clean atmosphere, showing a point of light when striking an opaque surface. The laser pointer may be a class II or class IIIa laser pointer.

In another embodiment, the light beam generator 14 may be an LED (light emitting diode) light. An LED is a semiconductor light source. LEDs are used as indicator lamps in many devices, and are increasingly used for lighting. Early LEDs emitted low-intensity red light, but modern versions are available across the visible, ultraviolet and infrared wavelengths, with very high brightness. As such, modern LED lights may produce light beams similar to the laser pointer described above.

In other embodiments, light beam generator 14 may generate other types of light sources, such as organic light emitting diodes (OLEDs), liquid crystal displays (LCDs), waveguides, traditional filament and fluorescent light bulbs, and any other light sources.

Figure 3:
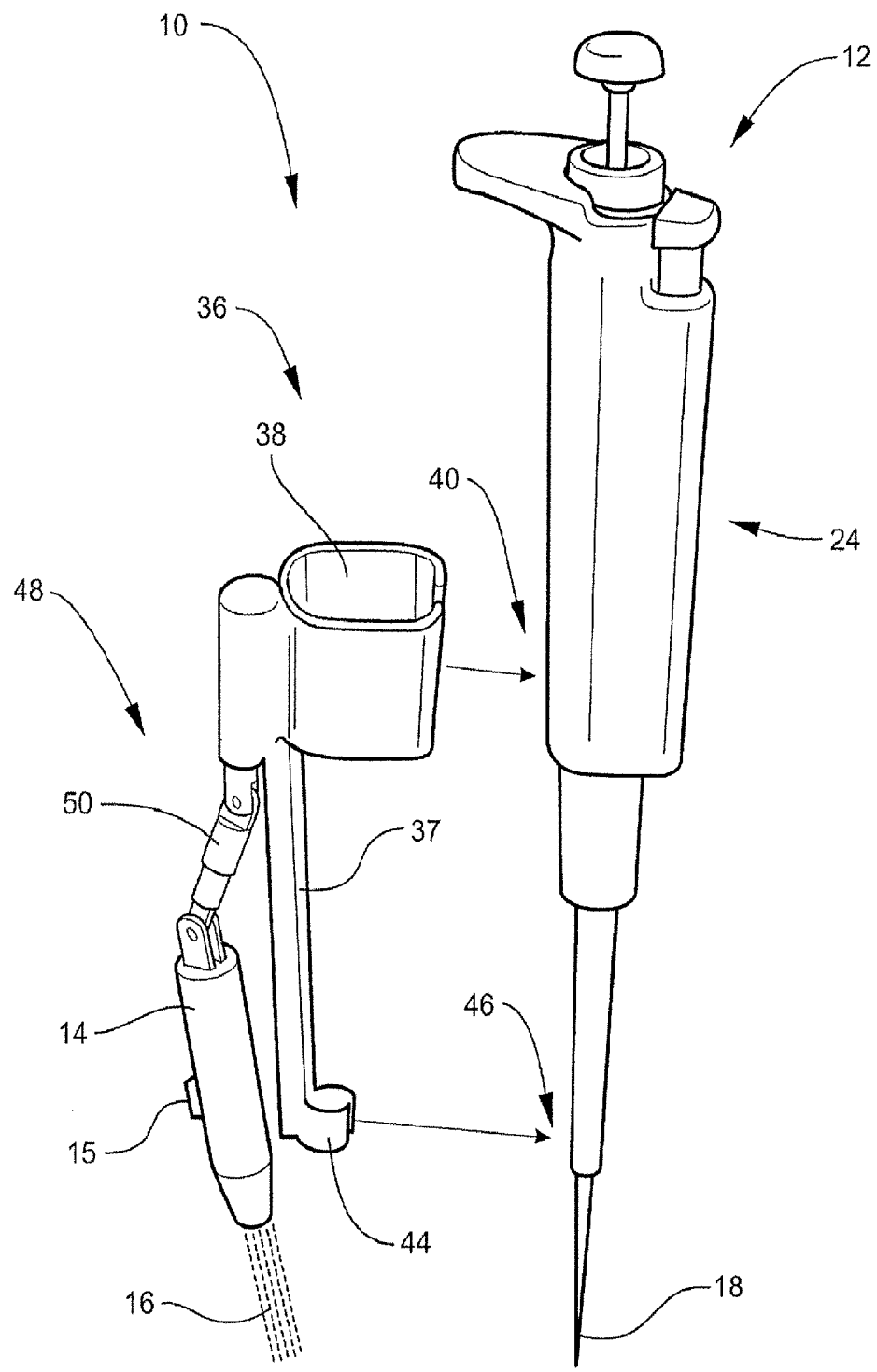
FIG. 3 is a perspective view of the light beam guided liquid delivery shown in FIG. 2 with the mount broken away.

Referring to FIGS. 2-3, the light beam guided liquid delivery device 10 is shown with light beam generator 14 mounted on the outside of an existing micropipette 24. In this embodiment, a mount 36 may be used to attach light beam generator 14 to the existing micropipette 24. Mount 36 may be any device capable of attaching light beam generator 14 to micropipette 24. Mount 36 may include, but is not limited to, tape, Velcro, an adhesive, a bracket, and any combinations thereof. A variety of materials are suitable for manufacturing all of these embodiments of the mount 36, however some uses will require the mount (and light beam generator) to be made of materials that can be autoclaved and/or cleaned with solvents that remove nucleic acids or other contaminants.

In one embodiment, mount 36 may include a bracket 37 adapted to connect light beam generator 14 to the outside of micropipette 24. Bracket 37 may connect light beam generator 14 by any means to micropipette 24. In one embodiment, bracket 37 may include a first clamp 38. First clamp 38 may be adapted to attach bracket 37 to micropipette 24 at a first connection point 40. First connection point 40 may be anywhere on micropipette 24, including the channel 42 of micropipette 24. First clamp 38 may be any device capable of connecting to the channel 42 of micropipette 42. In one embodiment, first clamp 38 may be a spring clip with a "c" shaped cross section, as shown in the Figures. Light beam generator 14 may be connected to bracket 37 approximate to first clamp 38.

In another embodiment, bracket 37 may optionally include a second clamp 44. Second clamp 44 may be adapted to attach bracket 37 to micropipette 24 at a second connection point 46. Second connection point 46 may be anywhere on micropipette 24, including an area approximate to tip 18. Second clamp 44 may be any device capable of connecting to the area approximate to tip 18 on micropipette 24. In one embodiment, second clamp 44 may be a spring clip with a "c" shaped cross-section, as shown in the Figures. Optional second clamp 44 may provide more stability to bracket 37 than an embodiment with just first clamp 38.

Figure 4:
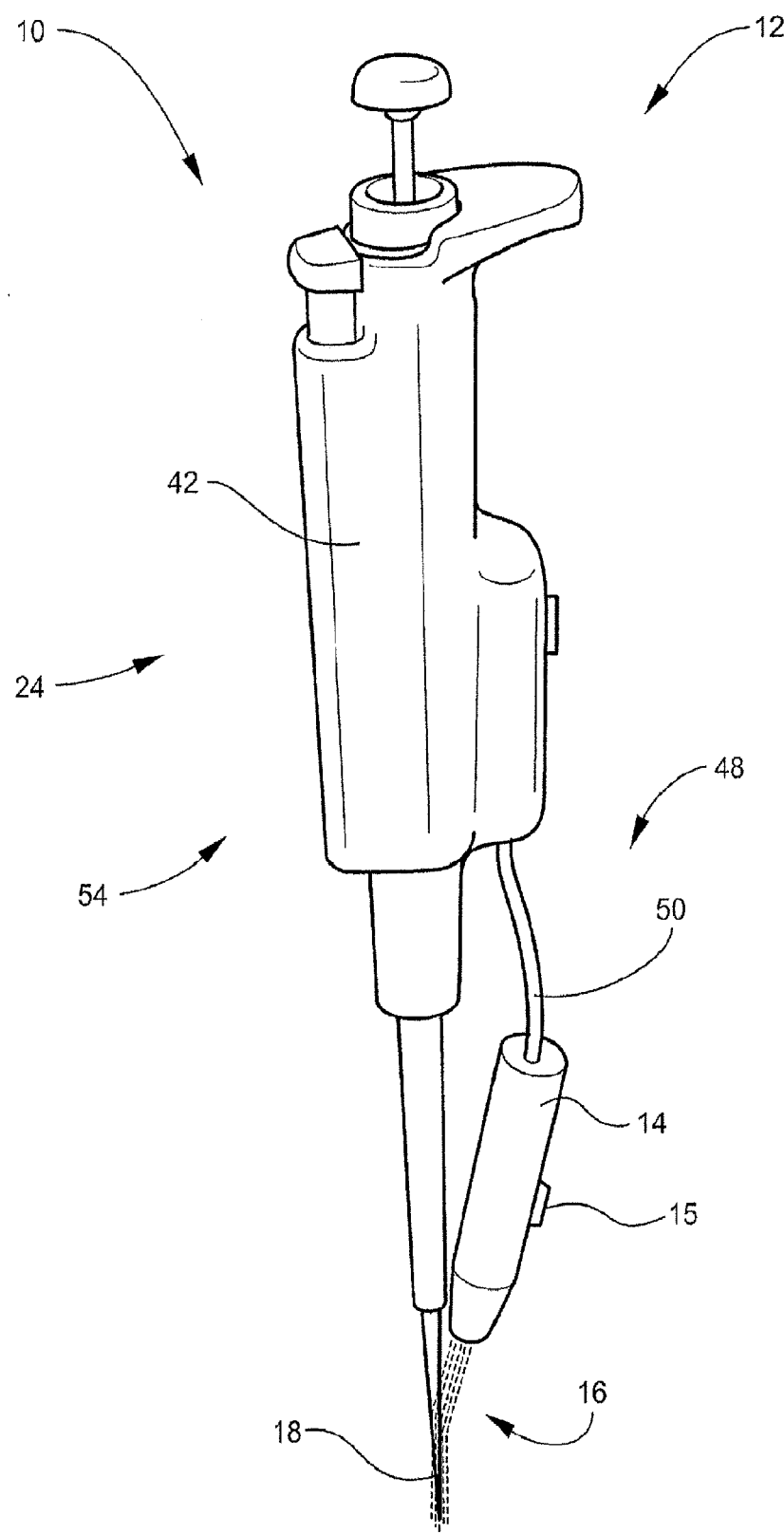
FIG. 4 a perspective view of another embodiment of the light beam guided liquid delivery device made according to the instant invention.

Bracket 37 may also include an adjustable connection 48 between first clamp 38 and light beam generator 14. Adjustable connection 48 may be for allowing the angle of light beam generator 14 to bracket 37 to be adjusted. This may allow for light beam 16 to be properly positioned below tip 18 of micropipette 24 (either directly or through tip 18 deflecting light beam 16). Adjustable connection 48 may allow the light path of light beam 16 to be directed below the various length and sizes of tip 18 that can be loaded onto micropipette 24 and that consequently highlights a target directly beneath tip 18 as shown in FIG. 2. In this embodiment, adjustable connection 48 allows the user to easily manually refocus and aim the laser beam to highlight solution delivery tips of varying lengths. In one embodiment, adjustable connection 48 may be a flexible wire 50, as shown in FIG. 4. Flexible wire 50 may allow for adjustment of light beam generator 14 in all directions. In another embodiment, adjustable connection 48 may be a plurality of bars 52 that are hingedly connected to one another, as shown in FIGS. 2-3. Plurality of bars 52 may include any number of bars, including, at least two. Providing at least two bars 52 may allow the angle of light beam generator 14 to bracket 37 to be adjusted as well as the distance light beam generator 14 may be positioned away from micropipette 24. Plurality of hinged bars 52 may allow for adjustment of light beam generator in one direction in the same plane as micropipette 24.

Referring to FIG. 4, the light beam guided liquid delivery device 10 is shown with light beam generator 14 mounted on the outside of a new micropipette 24. In this embodiment, light beam generator 14 may be integrally built onto the channel of micropipette 24.

Figure 5:
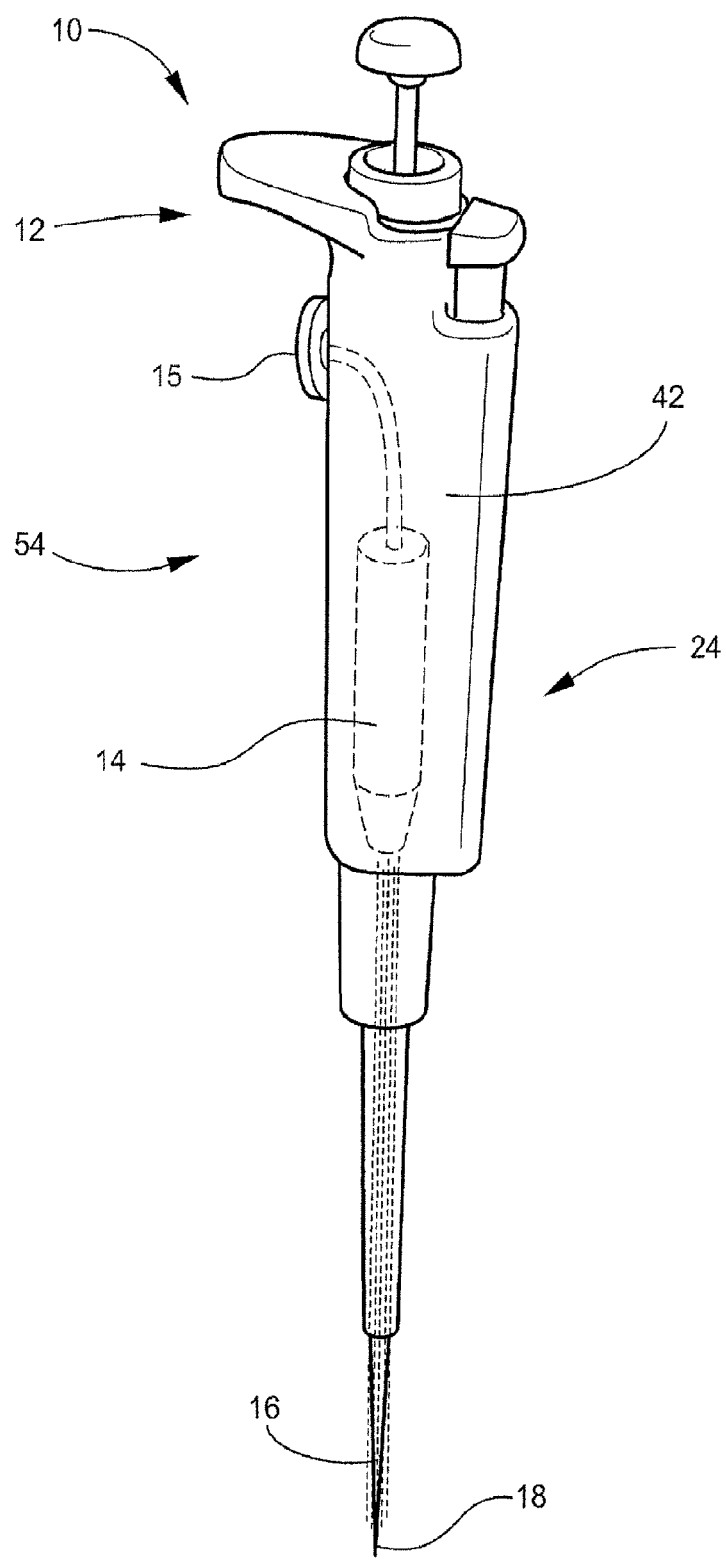
FIG. 5 is a perspective view of yet another embodiment of the light beam guided liquid delivery device made according to the instant invention.

Referring to FIG. 5, the light beam guided liquid delivery device 10 is shown with light beam generator 14 being manufactured on the inside of a new micropipette 24. In this embodiment, light beam generator 14 may be sealed on the inside of channel 42 of micropipette 24. Light beam generator 14 may be positioned to shoot light beam 16 straight down the barrel and out of tip 18. In this embodiment, button 15 may be wired to the outside of channel 42 for turning light beam 16 on or off. For the internal incorporations of the light beam generators 14 of the present invention, a focus device will be required, in order to allow the user to redirect the beam so that varying tip lengths can be used. This focus device may be wired to the outside of channel 42, and may be included with button 15.

The instant invention also includes a method of guiding the tip of a liquid delivery device with a guiding light beam. The method includes the steps of: providing light beam guided liquid delivery device 10 according to the instant invention; aiming light beam generator 14 to shoot light beam 16 below tip 18 of liquid delivery device 12; and tracking the placement of tip 18 of liquid delivery device 12 via light beam 16. The step of aiming light beam generator 14 may include aiming light beam 16 directly below tip 18, or may include aiming light beam 16 directly to the end of tip 18, where tip 18 redirects light beam 16 directly below tip 18.

The advantages to operators of the instant invention include reducing reagent pick-up and delivery error, and improving efficiency by speeding up the transfer of solutions by making it easier for the technician to visualize locations. A common pipetting error is placing a clear liquid in the wrong well of a clear or translucent plate. By highlighting the target and tip together, the technician can better see what is happening. A very similar situation arises when loading gels for electrophoresis. In this situation, the gels are clear or translucent, the tips are clear or translucent, and the solutions are clear or translucent, thus, highlighting the tip makes delivery of the solution into the well easier because it is easier to track the actual location. In all of these cases, the instant invention of a light beam guided liquid delivery device may be a great benefit to any lab, from those at research institutions such as universities, to commercial testing and government labs that are processing sensitive medical and forensic diagnostics samples, where some or all of the steps are performed by technicians rather than on robotic stations.

The present invention may be embodied in other forms without departing from the spirit and the essential attributes thereof, and, accordingly, reference should be made to the appended claims, rather than to the foregoing specification, as indicated the scope of the invention.

We claim:

1. A light beam guided liquid delivery device for tracking the placement of a sample by a liquid delivery device into a receptacle comprising:
    a micropipette having a channel with an exterior grip, a tip at one end and a plunger at its other end; and
    a light beam generator being mounted on the outside of said micropipette via a mount;
    said mount comprising:
        a clamp being adapted to attach said mount to said micropipette on said exterior grip of said channel;
        a second clamp being adapted to attach said mount to said micropipette at a second connection point being approximate to said tip of said micropipette;
        wherein, said light beam generator being connected to said mount approximate to said clamp; and
        said light beam generator being adapted to shoot a light beam on or below said tip of said micropipette, whereby, a user may track the placement of said tip of said micropipette via said light beam.

2. The light beam guided liquid delivery device of claim 1 wherein said light beam generator being aimed at said tip of said micropipette where said tip deflecting said light beam directly below said tip, thereby illuminating said tip and directly below said tip.

3. The light beam guided liquid delivery device of claim 1 wherein said micropipette being selected from the group consisting of: a manual micropipette, and an electronic micropipette.

4. The light beam guided liquid delivery device of claim 1 wherein said micropipette being selected from the group consisting of: a single channel micropipette, and a multi-channel micropipette.

5. The light beam guided liquid delivery device of claim 1 wherein said micropipette being an existing micropipette, whereby said light beam generator being mounted on the outside of said existing micropipette.

6. The light beam guided liquid delivery device of claim 1 wherein said mount further comprising an adjustable connection between said clamp and said light beam generator, said adjustable connection allowing the angle of said light beam generator to said mount to be adjusted.

7. The light beam guided liquid delivery device of claim 6 wherein said adjustable connection being a flexible wire.

8. The light beam guided liquid delivery device of claim 6 wherein said adjustable connection being a plurality of bars being hingedly connected to one another.

9. The light beam guided liquid delivery device of claim 1 wherein said light beam being a laser or an LED light.

10. A light beam guided liquid delivery device for tracking the placement of a sample by a liquid delivery device into a receptacle like a milliliter or microliter scale tube or a microtiter plate, comprising:
- a micropipette; and
- a light beam generator being mounted on the outside of said micropipette via a mount;
- said mount being adapted to mount said light beam generator on the outside of said micropipette and comprising:
  - a first clamp being adapted to attach said mount to said micropipette at a first connection point being approximate to a channel of said micropipette; and
  - a second clamp being adapted to attach said mount to said micropipette at a second connection point being approximate to a tip of said micropipette;
- wherein, said light beam generator being connected to said mount approximate to said first clamp; and
- said light beam generator being adapted to shoot a light beam below said tip of said micropipette, whereby, a user may track the placement of said tip of said micropipette via said light beam.

* * * * *